US009892576B2

(12) United States Patent
Kursun et al.

(10) Patent No.: US 9,892,576 B2
(45) Date of Patent: Feb. 13, 2018

(54) BIOMETRICS IDENTIFICATION MODULE AND PERSONAL WEARABLE ELECTRONICS NETWORK BASED AUTHENTICATION AND TRANSACTION PROCESSING

(71) Applicant: JP Morgan Chase Bank, N.A., New York, NY (US)

(72) Inventors: Eren Kursun, New York, NY (US); Gene Fernandez, New York, NY (US); Alex Berson, New York, NY (US); Brian Goodman, New York, NY (US)

(73) Assignee: JPMorgan Chase Bank, N.A., New York, NY (US)

( * ) Notice: Subject to any disclaimer, the term of this patent is extended or adjusted under 35 U.S.C. 154(b) by 308 days.

(21) Appl. No.: 14/077,869

(22) Filed: Nov. 12, 2013

(65) Prior Publication Data

US 2015/0035643 A1 Feb. 5, 2015

Related U.S. Application Data

(60) Provisional application No. 61/861,676, filed on Aug. 2, 2013, provisional application No. 61/886,474, filed on Oct. 3, 2013.

(51) Int. Cl.
*G07C 9/00* (2006.01)
(52) U.S. Cl.
CPC ..... *G07C 9/00134* (2013.01); *G07C 9/00158* (2013.01)
(58) Field of Classification Search
CPC .......................... G07C 9/00158; G07C 9/00134
(Continued)

(56) References Cited

U.S. PATENT DOCUMENTS 5,072,294 A 12/1991 Engle
5,229,764 A * 7/1993 Matchett ............ G07C 9/00158
340/5.52
(Continued)

FOREIGN PATENT DOCUMENTS

EP 2560123 2/2013
WO WO 2008/055181 5/2008
(Continued)

OTHER PUBLICATIONS

PCT International Preliminary Examination Report on Patentability, International Application No. PCT/US2014/048822, dated Feb. 11, 2016, pp. 1-8.
(Continued)

*Primary Examiner* — Edwin Holloway, III
(74) *Attorney, Agent, or Firm* — Hunton & Williams LLP

(57) ABSTRACT

Biometrics identification module and personal wearable electronics network based authentication and transaction processing are disclosed. According to one embodiment, a method for biometric authentication may include (1) a biometric identification device connecting to a plurality of sensing devices, each of the plurality of sensing devices receiving a user characteristic from a user; (2) the biometric identification device receiving the user characteristics from the sensing devices; (3) the biometric identification device communicating the received user characteristics to a server; (4) the biometric identification device receiving a biometric profile for the user; and (5) the biometric identification device storing the biometric profile.

15 Claims, 8 Drawing Sheets

(58) Field of Classification Search
USPC .................................................. 340/5.52, 5.82
See application file for complete search history.

(56) References Cited

U.S. PATENT DOCUMENTS

| | | | |
|---|---|---|---|
| 5,648,648 A * | 7/1997 | Chou | G07F 7/10 235/375 |
| 6,532,459 B1 | 3/2003 | Berson | |
| 6,697,942 B1 | 2/2004 | L'Heureux et al. | |
| 7,174,323 B1 | 2/2007 | Schultz et al. | |
| 7,330,570 B2 | 2/2008 | Sogo | |
| 7,360,239 B2 | 4/2008 | Mandalia et al. | |
| 7,454,470 B1 | 11/2008 | Isaacs | |
| 8,065,175 B1 | 11/2011 | Lewis | |
| 8,191,126 B2 | 5/2012 | Raghavan | |
| 8,606,611 B1 | 12/2013 | Fedorov | |
| 8,724,910 B1 | 5/2014 | Pillai | |
| 8,892,461 B2 | 11/2014 | Lau et al. | |
| 9,280,715 B2 | 3/2016 | Stephanson | |
| 2001/0036300 A1 | 11/2001 | Xia | |
| 2002/0138742 A1* | 9/2002 | Hamid | G06F 21/32 713/186 |
| 2002/0140542 A1* | 10/2002 | Prokoski | G06K 9/00885 340/5.52 |
| 2002/0174344 A1 | 11/2002 | Ting | |
| 2002/0180586 A1 | 12/2002 | Kitson et al. | |
| 2002/0198731 A1 | 12/2002 | Barnes | |
| 2003/0031348 A1 | 2/2003 | Kuepper et al. | |
| 2003/0046228 A1* | 3/2003 | Berney | G06F 21/32 705/41 |
| 2003/0210808 A1 | 11/2003 | Chen | |
| 2004/0098481 A1 | 5/2004 | Gunji | |
| 2004/0104266 A1 | 6/2004 | Bolle | |
| 2004/0111313 A1 | 6/2004 | Ingman | |
| 2004/0199663 A1 | 10/2004 | Horvitz | |
| 2004/0228504 A1 | 11/2004 | Chang | |
| 2005/0018883 A1* | 1/2005 | Scott | G06Q 20/382 382/115 |
| 2005/0108351 A1 | 5/2005 | Naick | |
| 2005/0138391 A1 | 6/2005 | Mandalia et al. | |
| 2005/0144560 A1 | 6/2005 | Gruen | |
| 2006/0010217 A1 | 1/2006 | Sood | |
| 2006/0095369 A1 | 5/2006 | Hofi | |
| 2006/0227997 A1 | 10/2006 | Au et al. | |
| 2006/0248344 A1 | 11/2006 | Yang | |
| 2006/0259778 A1 | 11/2006 | Gudorf | |
| 2007/0271341 A1 | 11/2007 | Kumar | |
| 2008/0126951 A1 | 5/2008 | Sood et al. | |
| 2008/0253622 A1 | 10/2008 | Tosa et al. | |
| 2008/0302870 A1 | 12/2008 | Berini | |
| 2009/0182822 A1 | 7/2009 | O'Sullivan | |
| 2009/0222913 A1 | 9/2009 | Fujii | |
| 2009/0252383 A1 | 10/2009 | Adam et al. | |
| 2009/0265106 A1 | 10/2009 | Bearman | |
| 2010/0011428 A1 | 1/2010 | Atwood | |
| 2010/0030798 A1 | 2/2010 | Kumar et al. | |
| 2010/0067745 A1 | 3/2010 | Kovtun et al. | |
| 2010/0169958 A1 | 7/2010 | Werner et al. | |
| 2010/0251359 A1 | 9/2010 | Shirai | |
| 2010/0287382 A1 | 11/2010 | Gyorffy et al. | |
| 2010/0321156 A1 | 12/2010 | Pitt | |
| 2011/0072039 A1 | 3/2011 | Tayloe | |
| 2011/0072510 A1 | 3/2011 | Cheswick | |
| 2011/0178962 A1 | 7/2011 | Sood | |
| 2011/0208716 A1 | 8/2011 | Liu et al. | |
| 2012/0023574 A1 | 1/2012 | Osborn et al. | |
| 2012/0068820 A1* | 3/2012 | Mollicone | G06F 21/00 340/5.82 |
| 2012/0151377 A1 | 6/2012 | Schultz et al. | |
| 2012/0157042 A1 | 6/2012 | McCanna | |
| 2012/0158798 A1 | 6/2012 | Patil | |
| 2012/0167199 A1 | 6/2012 | Riddiford | |
| 2012/0169461 A1 | 7/2012 | Dubois, Jr. | |
| 2012/0200567 A1 | 8/2012 | Mandel | |
| 2012/0255995 A1 | 10/2012 | Ahmed | |
| 2012/0291120 A1 | 11/2012 | Griffin | |
| 2012/0319817 A1 | 12/2012 | Abe | |
| 2013/0055362 A1 | 2/2013 | Rathbun | |
| 2013/0117059 A1 | 5/2013 | Norton et al. | |
| 2013/0262333 A1 | 10/2013 | Wicker | |
| 2013/0268775 A1 | 10/2013 | Hawkins | |
| 2013/0340061 A1 | 12/2013 | Tsukamoto | |
| 2013/0346067 A1 | 12/2013 | Bhatt | |
| 2014/0002238 A1 | 1/2014 | Taveau | |
| 2014/0007185 A1 | 1/2014 | Han et al. | |
| 2014/0096196 A1 | 4/2014 | O'Connor | |
| 2014/0137221 A1 | 5/2014 | Dominic et al. | |
| 2014/0181956 A1 | 6/2014 | Ahn et al. | |
| 2014/0268243 A1 | 9/2014 | Mitsubori | |
| 2014/0270404 A1 | 9/2014 | Hanna | |
| 2014/0347479 A1 | 11/2014 | Givon | |
| 2014/0363058 A1 | 12/2014 | Emmett | |
| 2015/0039527 A1 | 2/2015 | Hanna | |
| 2015/0200899 A1 | 7/2015 | Sanketi | |

FOREIGN PATENT DOCUMENTS

| | | |
|---|---|---|
| WO | WO 2009/067738 | 6/2009 |
| WO | WO 2012/164385 | 12/2012 |

OTHER PUBLICATIONS

European Patent Office Communication and Supplementary European Search Report, European Patent Application No. 14794941.6, dated Nov. 18, 2016, pp. 1-8.

* cited by examiner

BIOMETRICS IDENTIFICATION MODULE AND PERSONAL WEARABLE ELECTRONICS NETWORK BASED AUTHENTICATION AND TRANSACTION PROCESSING

RELATED APPLICATIONS

This patent application is related to the following applications: U.S. Patent Provisional Patent Application Ser. No. 61/861,676 filed Aug. 2, 2013, and U.S. Patent Provisional Patent Application Ser. No. 61/889,474 filed Oct. 3, 2013, the disclosures of which are hereby incorporated, by reference, in their entireties.

BACKGROUND OF THE INVENTION

1. Field of the Invention

The present invention generally relates to biometric authentication, and, more particularly, to a biometrics identification module and personal wearable electronics network based authentication and transaction processing.

2. Description of the Related Art

Biometric data has been used to identify people. One of the most popular uses is fingerprinting. As electronic fingerprinting becomes more popular, the risk of a misuse of this data is apparent.

SUMMARY OF THE INVENTION

Biometrics identification module and personal wearable electronics network based authentication and transaction processing are disclosed.

According to one embodiment, a method for biometric authentication may include (1) a biometric identification device connecting to a plurality of sensing devices, each of the plurality of sensing devices receiving a user characteristic from a user; (2) the biometric identification device receiving the user characteristics from the sensing devices; (3) the biometric identification device communicating the received user characteristics to a server; (4) the biometric identification device receiving a biometric profile for the user; and (5) the biometric identification device storing the biometric profile.

In one embodiment, connecting to a plurality of sensing devices may include the biometric identification device verifying that each of the plurality of sensing devices is registered to the user.

In one embodiment, the method may further include the biometric identification device sensing a user characteristic from the user.

The sensing device may be a wearable medical device, a microphone, a wearable electronic, a camera, etc. In one embodiment, the biometric identification device may communicate with at least one of the sensing devices by RF communication.

According to another embodiment, a biometric identification device is disclosed. The biometric identification device may include a personal identification module that stores a profile for a user; a static biometric identification module that stores at least one static user characteristic; a dynamic biometric identification module that stores at least one dynamic user characteristic; and a security engine that determines an amount of at least one of the static characteristics, the dynamic characteristics and the profile that can be communicated to a third party; and a transaction processing module that communicates the determined amount of at least one of the static characteristics, the dynamic characteristics and the profile to the third party.

In one embodiment, The biometric identification device may include a computer processor.

In another embodiment, the biometric identification device may communicate with a host device that comprises a computer processor. The host device may be a computer, a smart phone, etc.

In one embodiment, the biometric identification device may also include a field programmable module.

In one embodiment, the biometric identification device may also include a biometric data history table that may store a history of biometric activity.

In one embodiment, the dynamic biometric identification module further receives at least one user characteristic from at least one sensing device. The at least one sensing device may be a wearable medical device, a microphone, a wearable electronic, etc.

In one embodiment, the dynamic biometric identification module may communicate with at least one of the sensing devices by RF communication.

In one embodiment, a method for biometric authentication to conduct a transaction with a party, may include (1) a biometric identification device receiving a transaction request and biometric data from a user; (2) the biometric identification device determining a target level of biometric authentication required to conduct a transaction; (3) the biometric identification device determining biometric information necessary for the target level of biometric authentication; and (4) the biometric identification device transmitting the determined information to the party.

In one embodiment, the method may further include: prior to transmitting the determined information, the biometric identification device receiving approval to transmit the determined information to the party.

In one embodiment, the target level of biometric authentication may be based on at least one of a transaction amount and a security level associated with the transaction.

In one embodiment, the transaction may be an access to a restricted area.

In one embodiment, the biometric identification device may include a computer processor.

In one embodiment, the biometric identification device may communicate with a host device that comprises a computer processor.

In one embodiment, a biometric identification module that automatically authenticates user identity through background data acquisition and/or data acquisition/coordination with wearable or personal electronic devices s disclosed.

In another embodiment, a biometric auto authentication technique that uses profile and/or biometrics data acquired from user, authentication confirmation from personal or wearable electronic devices, or biometrics or profile data collected from users personal or wearable electronic devices is disclosed.

In another embodiment, techniques to combine the data from user, a range of biometric, personal or wearable electronic devices and authentication levels to perform authentication at the target security level are disclosed.

In another embodiment, techniques to perform a combination of offline and online authentication techniques to reach a target security level for authentication are disclosed.

In another embodiment, techniques to security authenticate a user or process a transaction by using existing authentication of the user from various personal and wearable devices based on their security and trustability specification are disclosed. In another embodiment, techniques to combine the authentication confirmations to match the target security level, even if the individual devices do not provide sufficient level individually, are disclosed.

In one embodiment, a biometric identification module may be implemented in a personal or wearable electronic device, a SIM-card like card, a chip that may be dedicated or embedded in other device, etc.

In one embodiment, sensors and other data acquisition devices may be used that capture, for example, voice, a user's face or other image, video, any user electrical or chemical profile (e.g., electrocardiogram, brain waves/signals, skin resistance, acidity, heartbeat, pulse, breathing, etc.), an activity profile, movement characteristics, GPS data, a user's data characteristics, other behavioral characteristics (e.g., typing or touch screen patterns, etc.), etc. are disclosed.

In one embodiment, methods of generating a full user profile of the user based on multiple and potentially disparate pieces of data acquired from multiple wearable or personal devices, or through the biometric identification module itself, are disclosed.

In one embodiment, methods of continuous anomaly detection for spoofing or fraud through checking consistency of the acquired data with the user's full profile are disclosed.

In one embodiment, a biometric identification module may comprise a Personal ID module, a Static and Dynamic Biometric ID module, a Transaction Processing module, a Biometrics Data History Table, Security and Policy Engines, and a Field Programmable Module.

In one embodiment, two or more of the modules may interact. For example, the Security and Policy Engines may check that the biometrics data acquisition, processing and authentication matches the target security levels.

In one embodiment, a biometric identification module may processes transactions traditionally made by online temporary card IDs or traditional credit or debit cards is disclosed. For example, the biometric identification module may make payments, transfer funds with a range of external entities through the financial institution, etc.

In one embodiment, each transaction may reveal only sufficient information about the user to conduct the transaction, thereby protecting the user's personal privacy and biometrics privacy to process the transaction. The amount of information may be customized for each vendor based on, for example, how trusted the vendor is, nature of the transaction, etc.

In one embodiment, techniques to replace a user's personal credit card/bank card or other payment device with a biometric identification module are disclosed.

In one embodiment, techniques to make payments through a biometric identification module through a secure connection or offline mode trusted device connection with a financial institution are disclosed.

In one embodiment, techniques for full password replacement for online transactions using a biometric identification module is disclosed. In one embodiment, the user's financial institution may mediates the transaction to protect the user's privacy.

In one embodiment, techniques for customized identity verification or transaction processing with a range of privacy settings matching the requirements of the transaction are disclosed.

In one embodiment, techniques for full ID verification using a biometric identification module are disclosed.

In one embodiment, techniques for one-time online transaction hidden ID verification for purchases or other transactions are disclosed.

In one embodiment, techniques to protect a user's biometrics and transaction and user profile data if the a biometric identification module is separated from the user through multi-step sensing and reacting to separation are disclosed.

In one embodiment, techniques to detect that the device is separated from the user or the other biometrics devices through anomaly detection and continuous monitoring of users data in the background are disclosed.

In one embodiment, techniques to communicate potential fraud or spoofing through the detection of disconnect from the user to the financial institution and the user are disclosed.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF PREFERRED EMBODIMENTS

Figure 1:
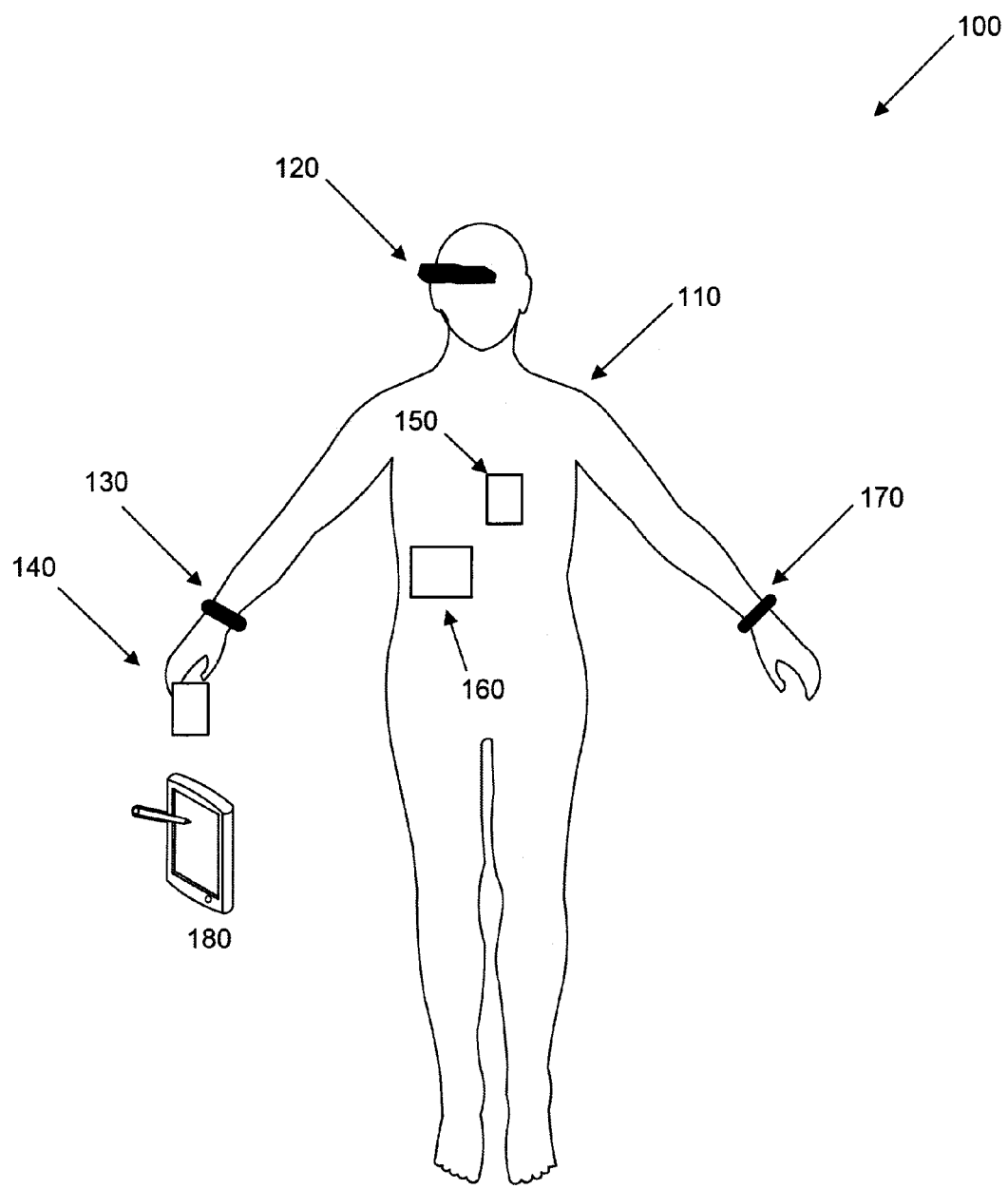
FIG. 1 is a block diagram of a system for biometric authentication using a wearable biometric network according to one embodiment.

Several embodiments of the present invention and their advantages may be understood by referring to FIGS. 1-8, wherein like reference numerals refer to like elements.

Embodiments relate to the receipt, processing, and use of data from wearable and/or implantable biometric devices, such as Google Glass, the "smart" watches, health bracelets, heart rate monitors, wearable glucose monitors, wearable EKG devices, wearable fitness bands, wearable activity monitors, electrochemical skin sensors, motion sensors, etc. One or more of these devices may provide user biometric data to a biometric identification module or device.

In one embodiment, the biometrics ID module/device may be a biometric ID card that may be similar to a SIM card. Such a card may be inserted into a wireless device, such as a smartphone, tablet, or similar device. The wireless device may then serve as a hub for authentication process and/or communication hub for medical data.

In another embodiment, the biometrics ID module/device may be a dedicated device or dedicated chip that may reside in a number of electronic devices, such as a smartphone, laptop computer, tablet computer, etc. In one embodiment, static biometrics and personal identification information may be hardcoded/hardwired into the chip.

In still another embodiment, the biometric identification device/module may be an application executed by a smartphone, laptop computer, tablet computer, etc.

In one embodiment, the biometric data that is transmitted between the wearable/implantable biometric devices may be encrypted.

In one embodiment, the biometrics identification device/module may control further transmission or release of the user's biometric data to any third party, such as a party authorizing access to an area, a party to a transaction, etc.

In one embodiment, the biometrics ID module/device may be used to authenticate the user to others, and the user may select the amount of information that the user wishes to disclose. For example, for high risk transactions, more information may be disclosed to the authenticating party. For low risk transactions, less information may be disclosed.

The biometrics ID module/device may be used to authenticate the user to a system and may be used in place of a user id and password.

In one embodiment, the biometrics ID module/device may also be directly linked to a primary bank account for transaction processing, replacing credit card or debit card, automatic authentication of banking transactions, authentication for online transactions with untrusted entities, etc. It may also replace and/or supplement, identification cards, such as a driver's license, an employee ID, etc.

In one embodiment, the biometrics ID module/device may be used to collect data for a "Big Data" marketplace whereby users have ownership of their own transaction and sensor data. A user may, for example, develop, sell, trade, delete, etc. his or her transaction and sensor data profile. The user may receive incentives (discounts, rewards, etc.) for doing so.

The system may further be used to authenticate the user in different environments. For example, biometric data may be received from the user, and a processor at the environment may determine the user's identity. In another embodiment, the identification of the devices (e.g., serial number, media access control (MAC) address, etc. may be used to authenticate the user. For example, if at least three devices that are registered to the user are in the same area, the user may be authenticated.

Referring to FIG. 1, a system for biometric collection is disclosed. System 100 includes several different biometric devices that may be worn by, or implanted within, user 110. Any device or combination of devices that sense and transmit biometric data for a user may be used. For example, eye scanner/imager 120, such as Google Glass, may be used. Eye scanner/imager 120 may capture an image of one or more of the user's irises, retinas, or other eye feature.

In one embodiment, eye scanner/imager 120 may further include a microphone for capturing the user's voice biometrics. Glucose monitor 130 (noninvasive and invasive) may be used to measure and transmit a user's blood sugar level. Smartphone 140 may be used to capture images of the user, voice biometrics, electrochemical signals from users skin, EKG signals, etc. A user's motion, behavioral profile, sleep profile, or any other activity profile may be captured.

Activity monitor 150, such as a heart rate monitor, a fitness band, etc. may be used. EKG device 160, which may be a portable device, an implantable device, etc. may be used. Smart watch 170 may also be used to capture a user's motions and other biometrics.

In one embodiment, one or more of the biometric devices may capture fingerprints, detect sleep patterns, detect moods, monitor exercise activity, etc. In general, any characteristic signal that may be used to identify the user, such as a chemical signal, an electrical signal, a motion signal, etc. For example, chemical analysis, or electrical analysis, of the skin may be performed using sensors (not shown). Electrical signals (such as brain waves, EKG signals, etc.) may be acquired through a collection of sensors (not shown). DNA may be collected and analyzed through sensors (not shown) and processing units (not shown).

System 100 may further include biometrics ID module/device 180. As noted above, biometrics ID module/device 180 may be any device that is capable of receiving data from the biometric sensing devices (e.g., elements 120-170). In one embodiment, biometrics ID module/device 180 may be a standalone device, and may acquire data itself. In another embodiment, biometrics ID module/device 180 may be an accessory for laptop computer, tablet computer, smartphone, etc. In still another embodiment, biometrics ID module/device 180 may be an application executed on a laptop computer, tablet computer, smartphone, etc.

In one embodiment, biometrics ID module/device 180 may be part of one of the biometric sensing device. For example, biometrics ID module/device 180 may be part of, or implemented by, eye scanner/imager 120, smartphone 140, smart watch 170, etc.

In one embodiment, biometrics ID module/device 180 may communicate with any of the biometric sensing devices (e.g., elements 120-170) by any suitable communication protocol, including wire-based communication, wireless communication (e.g., radio frequency, infrared, etc.). In one embodiment, some, or all, of the communications may be encrypted.

Biometrics ID module/device 180 may communicate with third parties, such as point of sale terminals (not shown), access points and devices (not shown), etc. In one embodiment, biometrics ID module/device 180 may be used for personal, social and identification purposes, such as the authentication of counterpart devices at one's home/property/car; the medical use devices at a hospital, during triage, or for first responders; in government functions, such as in a courtroom, with police, at border crossings, at customs, etc.

In one embodiment, the biometrics ID module/device 180 may perform the authentication process by itself. In another embodiment, supporting devices and data from such devices may be used for authentication.

Figure 2:
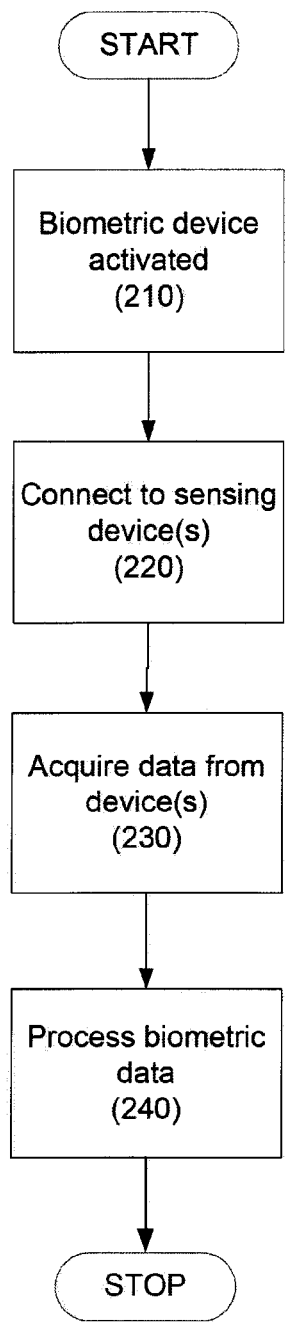
FIG. 2 is a high-level flowchart depicting a method for biometric authentication using a wearable biometric network according to one embodiment.

Referring to FIG. 2, a method of authentication using biometrics identification module according to one embodiment is provided. In step 210, a biometrics ID module/device, such as that described above, may be activated.

In step 220, the biometrics ID module/device, such as that described above, may connect with sensing devices, such as an eye scanner/imager, a fingerprint sensor, a microphone, an activity monitor, a glucose monitor, an EKG monitor, a motion sensor, a camera, etc. Any suitable communication may be used, such as wireless (e.g., near field communication, Bluetooth, WiFi, infrared, etc.), wired, etc.

In step 230, the biometrics ID module/device may acquire data from the sensing device(s). In one embodiment, biometrics ID module/device may also acquire data from the user.

In step 240, the biometrics ID module/device and/or a server may process the biometric data and other data. In one embodiment, the biometrics ID module/device and/or server may generate a biometric profile for the user. In another embodiment, the biometrics ID module/device and/or server may transmit some or all of the data to an authenticating authority. In another embodiment, the biometrics ID module/device and/or a server may authenticate the user. In still another embodiment, the biometrics ID module/device and/or a server may store some or all of the data.

Figure 3:
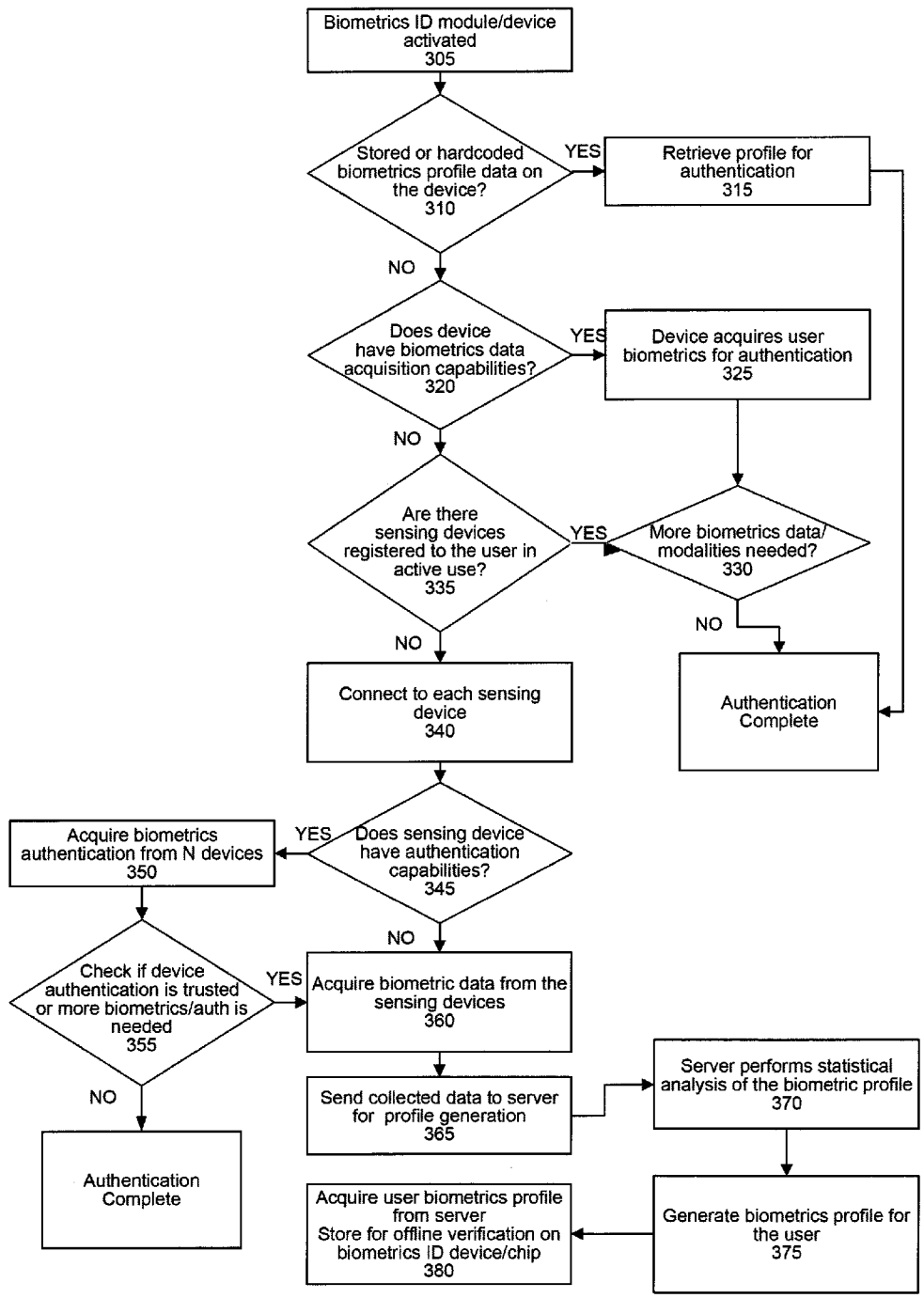
FIG. 3 is a flowchart depicting a method for biometric authentication using a wearable biometric network according to one embodiment.

Referring to FIG. 3, a method of authentication using biometrics identification module according to one embodiment is provided.

In step 305, a biometrics ID module/device, such as that described above, may be activated. In one embodiment, this may involve turning on a device, launching an icon, enabling communication with sensors and/or external devices, etc.

In step 310, a check is made by the biometrics ID module/device to see if there is a stored or hardcoded biometric profile on the device, chip, associated memory, etc.

If there is, in step 315, the profile is retrieved. This may be when, for example, the biometrics ID module/device has already authenticated the user and has stored authentication information on the device, etc.

In one embodiment, this may be a static implementation, where the user may have recently been authenticated. In another embodiment, this may be proximity based, such as the user has been authenticated successfully and has not disconnected or stepped away from the sensor, personal or wearable electronics, etc. Thus, the authentication continues to be valid.

In another embodiment, a biometrics ID module/device may be used very similar to an traditional identification card that does not require dynamic authentication process, so long as it resides with the user.

If not, in step 320, a check is made to see if the biometrics ID module/device has data acquisition capabilities. If it does, in step 325, the biometrics ID module/device acquires user biometrics for authentication.

In step 330, the biometrics ID module/device checks to see if additional biometrics data is necessary. For example, the biometrics ID module/device may determine whether or not it has sufficient data to perform the requested authentication, access, transaction, etc. If it is, in step 335, the biometrics ID module/device checks to see if there are sensing devices, such as an eye scanner/imager, fingerprint sensor, microphone, activity monitor, glucose monitor, EKG monitor, motion sensor, camera, etc., registered to the user that are in use.

For example, a smart watch may sense the user's EKG, movement profile, behavior profile. A device, such as Google Glass, may sense a user's iris profile, eye movement, behavioral profile, etc. A blood sugar monitor may monitor a user's blood sugar level, characteristics, etc. A wearable EKG device may sense the user's EKG signal. A mobile phone/"smart" phone may detect the user's behavioral biometrics, images, voice biometrics, etc.

In step 340, for each sensing device that the biometrics ID module/device may be connected to, the biometrics ID module/device may connect with the sensing device by any suitable protocol, including radio frequency (e.g., near field communication, Bluetooth, WiFi, etc.), infrared, etc.

In step 345, the biometrics ID module/device checks to see if each sensing device has authentication capabilities, indicating that the sensing device can authenticate the user through one or more modalities (such as iris recognition, face, voice recognition, signatures, pin/passwords, other forms of biometrics. For example, a "smart glass" or "smart watch" may be able to authenticate the user by itself. If such authentication is accepted, each device's confidence level and authentication security level may be considered. If it does, in step 350, the biometrics identification device acquires biometrics authentication from the devices. In one embodiment, the biometrics ID module/device may acquire data from the authenticating sensing devices, such as whether or not the user is authenticated, user profile information, confidence, accuracy and security scores, and other data that may be used for authentication.

In step 355, the biometrics ID module/device checks to see if the device authentication is trusted or not. In one embodiment, the biometrics ID module/device may use a collection of other devices' authentication results to authenticate the user. The confidence and accuracy scores for those devices may be considered.

In step 360, the biometrics ID module/device may acquire biometric data from the sensing devices. In one embodiment, real-time time-series user data may be received via, for example, near field communication, or any other suitable communication, with sensing devices.

In step 365, the biometrics ID module/device may provide the acquired biometric data to a server so that a biometric profile may be generated. In one embodiment, the data may be sent for multi-device biometrics profile generation.

In step 370, the server may perform statistical analysis of the biometric profile. For example, the server may determine normal biometric ranges for the user, extract unique personal markers and/or identifiers, perform anomaly detection, and may cross link multiple devices to generate integrated markers.

In step 375, the server may generate a biometric profile for the user. In one embodiment, a profile may be created for each sensing device. In another embodiment, an integrated biometric profile may be generated using some (e.g., a "snippet") or all of the data from a plurality of sensing devices.

In step 380, the biometrics ID module/device may receive the user's biometrics profile from the server. In one embodiment, it may store the profile for offline verification. In one embodiment, it may be stored in the biometrics ID module/device.

Figure 4:
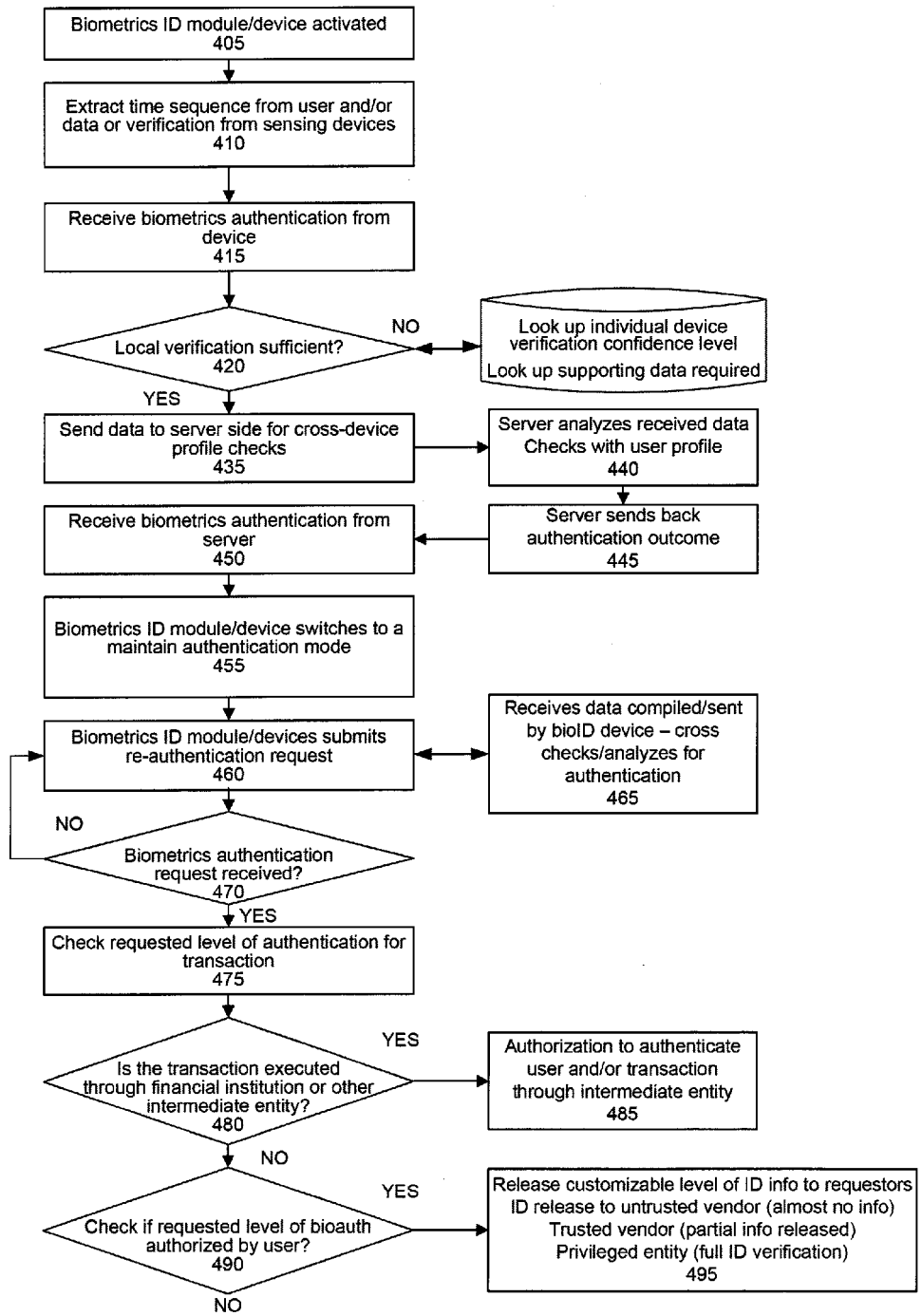
FIG. 4 is a flowchart depicting a method for biometric authentication using a wearable biometric network according to one embodiment.

Referring to FIG. 4, a method of authentication using biometrics identification module according to another embodiment is provided.

In step 405, a biometrics ID module/device, such as that described above, may be activated. In one embodiment, this may involve turning on a device, launching an icon, enabling communication with sensors and/or external devices, etc.

In step 410, the biometrics ID module/device may acquire data by at least one of acquiring biometrics or other profile data from user, acquiring biometrics or other data from sensing or personal devices, or acquiring existing authentication state from sensing and other personal devices.

In step 415, the biometrics ID module/device retrieves offline data is stored on the biometrics ID module/device.

In step 420, the biometrics ID module/device checks to see if the local data is sufficient for verification. If the local verification is sufficient, the verification confidence for individual devices may be retrieved from, for example, database 430. In addition, in one embodiment, the additional data may be retrieved from, for example, one or more sensing device, from the user directly, etc.

In step 435, data may be provided to the server for cross-profile check, and, in step 440, the server may analyze the data by checking the received data against a stored user profile. For example, in one embodiment, iris recognition may be sufficient. In another embodiment, fingerprint recognition may be required for additional biometric data.

In one embodiment, the sufficiency of data may be based on the security level for the transaction, authentication, etc. For example, if the user is attempting to wire a significant amount of money, the security clearance needed may be different than the level used for a simple low-risk transaction. As another example, different applications can have different security levels. Medical applications, identification applications, government applications, etc. may require high levels of security, which means additional biometric data may be needed, while simple password replacement application for a social media site for instance may not require a high level of security.

In step 445, the server may return the results of its authentication check, and in step 450, the biometrics ID module/device may receive the results.

In step 455, if the server returns a result indicating that the user is authenticated, the biometrics ID module/device then switches to maintain authentication mode. In one embodiment, the authentication may continue to execute in the background.

In step 460, the biometrics ID module/device may periodically, randomly, etc. or when an anomaly is detected, request re-authentication, or an authentication check, from the server. For example, in step 465, the server may receive data from the biometrics ID module/device, and may cross/check and/or analyze the data for authentication. This may be similar to step 440, above.

In one embodiment, the server may return the results of the authentication check. In another embodiment, the server may return the results of it authentication check only if the check fails.

If, in step 470, a request for biometrics authentication is received from a third party, for example, a point of sale device, an access point, etc., in step 475, the biometrics ID module/device may check the level of authentication required for the transaction. In one embodiment, the third party may specify the level of authentication required. In another embodiment, the user may specify the amount of authentication required.

In step 480, if the transaction is executed through an intermediate entity (e.g., a financial institution), in step 485, the biometrics ID module/device may request authorization to authenticate the user and/or transaction through the intermediate entity.

If, in step 490, the requested level of biometric authorization is authorized by the user, in step 495, the biometrics ID module/device may release up to the authorized amount of biometrics data to the requester. In one embodiment, for an untrusted vendor, little data, such as the user's name, transaction references, etc. may be released. For a trusted vendor, partial information may be released, such as a user's historical transaction profile with the vendor. For a privileged entity, such as a financial institution government institution, etc., full biometric information may be released. The amount of data released may vary depending on the specific party and/or the nature of the transaction. For example, the user's identity confirmation or other transaction data may be released In some cases, however, the user's identity maybe concealed, and only transaction data may be released.

Figure 5:
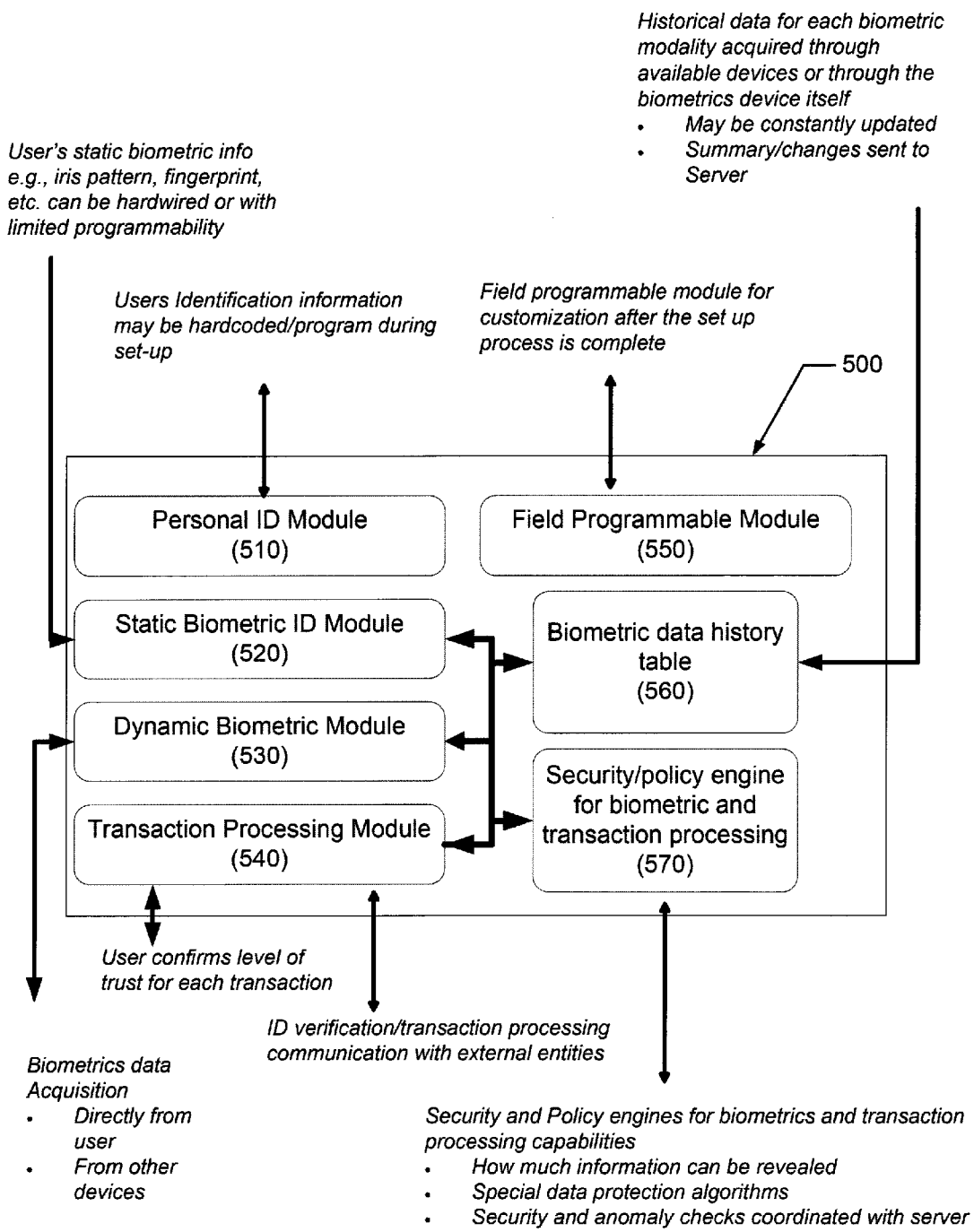
FIG. 5 is a block diagram of a biometrics ID module/device according to one embodiment.

Referring to FIG. 5, a block diagram of a biometrics ID module/device is provided. Biometrics ID module/device 500 may include a personal identification module 510, static biometric identification module 520, dynamic biometric module 530, transaction processing module 540, field programmable module 550, biometric data history table 560, and security/policy engine(s) 570. In one embodiment, static biometric identification module 520, biometric data history table 560 and dynamic biometric module 530 may communicate to receive biometric and/or other sensor data and check that data with a static profile and a historic profile for the user. Transaction processing module 540 may then use the outcome of this cross module authentication process to authenticate the user and execute transactions via coordinating with server side counter parts. In one embodiment, transactions may be financial transactions, such as money transfers/wires or external vendor transactions such as purchases, etc.

Personal identification module 510 may contain basic identifying information for the user (or users). For example, it may store the user's name, height, eye color, social security number, weight, etc. Additional information, or less information, may be stored as necessary and/or desired.

Static biometric module 520 may receive and/or store a user's static biometric information, such as an iris pattern, fingerprint, etc. In one embodiment, this information may be "hardwired" (e.g., burned into the chip, in a ROM, etc. or may have limited programmability.

Dynamic biometric module 530 may acquire biometric data from the user, from a biometric sensing device (e.g., medical device), wearable electronics, mobile electronic devices (e.g., smartphones, etc.).

Transaction processing module 540 may be used to communicate with external entities in order to verify the user's identity or conduct a transaction. In one embodiment, the user may confirm the level of "trust" for each transaction and/or communication. For example, the user may confirm the amount of personal information that biometrics ID module/device 500 shares with the external entities. A user may choose to share more information with a trusted entity, such as a bank or government institution, than with a non-trusted entity, such as a vendor.

Field programmable module 550 may be used for customization after the set-up process is completed. In-field customizations may be enabled through the field programmable arrays incorporated in the biometrics ID module/device 500. This dynamic updating capability may be used for adapting to the new security policies, users profile or biometric modality changes.

Biometric data history table 560 may store historical data for each biometric modality. For example, it may store historical data from each biometric sensing device, from the device itself, etc. In one embodiment, biometric data history table 560 may be continuously updated as biometric data is acquired. In another embodiment, biometric data history table 560 may be updated periodically or as necessary and/or required.

In one embodiment, updates to the biometric data history table 560 may be provided to the server. In one embodiment, any updated outside of a predetermined threshold may be provided as an alert to the server. In another embodiment, updates to the biometric data history table 560 may be provided to the server as necessary and/or desired.

Security/policy engines 570 for biometric and transaction processing may identify the amount of biometric and/or personal data that may be revealed, transmitted, etc. to external entities. In one embodiment, engines 570 may execute data protection algorithms such as specialized encryption algorithms for different types of biometrics or transaction data, may implement different security algorithms for different types of transactions, etc.

Security/policy engines 570 may also check the data integrity of the sensing devices, such as wearable personal devices, cell phones, smart watch, smart glass etc. as well as authentication accuracy of the individual devices with such capability. For example, there may be a 90% authentication confidence rate for an iris scanner in the smart glass device, while a blood glucose monitor may have only a 30% confidence rate. The resulting authentication may depend on the type of authentication verifications received from different devices, their accuracy levels and overall evaluation of the data for data integrity. Security/policy engines 570 may then authenticate the user (in some embodiments cross-checking with server side as well) and permit transaction processing module 540 to execute the requested transactions or authentication requests.

Security/policy engines 570 may also provide security and/or anomaly checks. For instance, if a biometric that is received by a biometric sensing device is received that is anomalous, indicating potential fraud, engines may increase security by, for example, receiving additional biometric data, limiting authentication and/or transactions, etc.

Security/policy engines 570 may also cross-checks the data across different modules. For example, security/policy engines 570 may static data stored in the static biometric module 520 against data acquired by dynamic biometric module 530, historical data in biometric data history table 560, etc. for consistency.

In one embodiment, engines 570 may coordinate with servers. For example, in one embodiment, the server may issue warnings or change security policies in response to detected threats. In another embodiment, engines 570 may coordinate how much information may be revealed, security level, etc. In another embodiment, engines 570 may coordinate special data protection algorithms. In still another embodiment, engines 570 may coordinate security and anomaly checks.

In one embodiment, biometrics ID module/device 500 may directly acquire user profile data, or may use trusted personal mobile device authentication. For example, biometrics ID module/device 500 may use fingerprint authentication from, for example the iPhone 5s.

Biometrics ID module/device 500 may be implemented as a "BID," or Biometrics Identification card. In one embodiment, this may be similar to a SIM card, and may be inserted to the users mobile device, tablet computer, etc. This may make the device a hub for authentication process and/or communication hub for medical data that may use the host device's communication capability.

In another embodiment, biometrics ID module/device 500 may be implemented as a dedicated device, dedicated chip, etc. that may reside in number of personal devices. In one embodiment, static biometric, personal identification information, etc. can be hardcoded/hardwired into the card, chip, etc.

In one embodiment, biometrics ID module/device 500 may have embedded security module to protect the user's identity and to implement security policies.

In one embodiment, biometrics ID module/device 500 may be directly linked to a primary bank account for transaction processing. In another embodiment, biometrics ID module/device 500 may replace a credit card or debit card. In another embodiment, biometrics ID module/device 500 may be used for automatic authentication of banking transactions. In still another embodiment, biometrics ID module/device 500 may provide authentication for online transactions with untrusted entities. In yet another embodiment, biometrics ID module/device 500 may be used as an identification card, such as a driver's license, a TSA "Pre-check" card, passports, an employee identification card, a library card, a membership card, a building/area access card, etc. In one embodiment, biometrics ID module/device 500 may release biometrics data to external entities. This may be subject to user authorization.

In one embodiment, biometrics ID module/device 500 may include an interface (not shown). In one embodiment, the interface may communicate with biometric sensing devices, personal electronic devices, etc. In another embodiment, the interface may communicate with devices for external entities. In still another embodiment, the interface may enable the biometrics ID module/device 500 to communicate with a host device, such as a smartphone, table computer, etc. For example, the interface may be a SIM card-type interface, a USB interface, etc. Any suitable interface may be used as necessary and/or desired.

Figure 6:
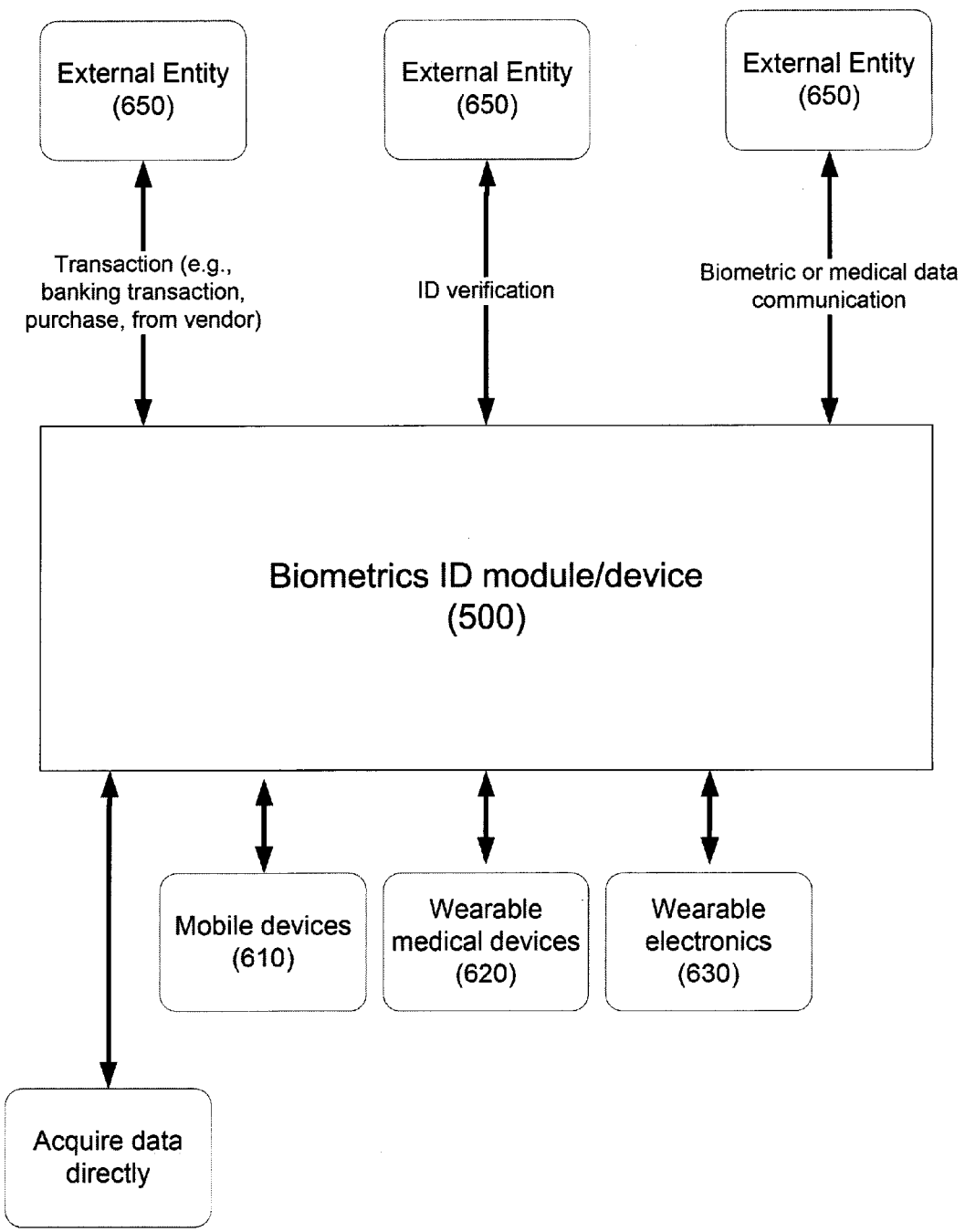
FIG. 6 is a diagram depicting interactions with a biometrics ID module/device according to one embodiment.

Referring to FIG. 6, a diagram of interactions with a biometrics ID module/device is provided according to one embodiment. Biometrics ID module/device 500 may interface with mobile devices 610, wearable medical devices 620, wearable electronics 630, etc. in order to receive biometric and/or other personal data from the user. In addition, biometrics ID module/device 500 may receive biometric and/or other personal data directly from the user.

For example, biometrics ID module/device 500 may acquire face recognition data, voice recognition data, iris recognition data, fingerprint data, behavioral data (e.g., movement, etc.), and device profile data. For example, biometrics ID module/device 500 may include cameras, microphones, touch sensors, motion sensors, chemical sensors, electrical sensors, etc. that may be used to collect the biometric and/or other data from the user.

Mobile devices 610 may acquire biometric and/or other data from the user, such as face recognition data, voice recognition data, iris recognition data, fingerprint data, behavioral data (e.g., movement, etc.), and device profile data. For example, mobile devices 610 may include cameras, microphones, touch sensors, motion sensors, etc. that may be used to collect the biometric and/or other data from the user.

Wearable medical devices 620 may acquire biometric data from the user, such as an EKG signal, an electrical/chemical data from the skin, blood glucose data, heart rate, thermal profile data, etc.

Wearable electronics 630 may acquire biometric and/or other data from the user, such as movement data, GPS profile data, thermal profile data, behavioral profile data, etc.

Biometrics ID module/device 500 may communicate with external entities 650 to, for example, authenticate the user, conduct transactions, etc. For example, biometrics ID module/device 500 may conduct a transaction (e.g., purchase an item from a vendor, conduct a banking transaction) with external entity 650. Biometrics ID module/device 500 may also verify an identification of the user with external entity 650. Biometrics ID module/device 500 may also communicate the user's biometric of medical data to external entity 650.

Biometrics ID module/device 500 may control the amount of data that is shared with each external entity 650. In one embodiment, the amount of data shared may be based, for example, on the level of trust with external entity 650. For a more trusted external entity 650, more data may be shared; for a less trusted external entity 650, less data may be shared.

In one embodiment, a "marketplace" of biometric data may be created. For example, biometric authentication may replace password-based authentication. Releasing biometric information, however, in all instances of password replacement may be undesirable as it may create a security risk.

Thus, a trusted biometrics authentication provider may serve to authenticate a user to a vendor or other transaction participant.

For example, a biometric based trusted authentication channel may be used for private shopping. In one embodiment, the user may be authenticated with the trusted financial party through biometrics ID module/device, and then the trusted financial institution may releases payment to the online vendor without releasing detailed personal info, user accounts passwords, etc.

For a bank or financial institution that can provide hashing capabilities to enhance user privacy, the user may release his or her full biometric profile.

In one embodiment, the biometrics ID module/device may provide continuous and user-friendly authentication using biometric data and/or other data. In one embodiment, the biometrics ID module/device may execute on a mobile device, which may or may not be wearable.

When the biometrics ID module/device is separated from the user, the biometrics ID module/device is at risk of being tampered with and/or "spoofed" (such as being connected to another person's biometric/medical/wearable devices, tampering with the hardware, tampering with the software, etc.

To address this, the biometrics ID module/device may go into a higher-security inactive mode when the user is separated from the biometrics ID module/device. For example, the biometrics ID module/device may take a proactive security action, such as self-wiping, deletion of files/certificates, etc. if a spoofing attack or high-risk event is detected.

In one embodiment, the biometrics ID module/device may include dedicated hardware and/or software to protect the biometrics ID module/device.

In one embodiment, the biometrics ID module/device may constantly monitor the biometrics markers through wearable devices, biometrics data, phone records, etc. The biometrics ID module/device may dynamically update the user's profile data and identify anomalies.

If biometrics authentication fails, the additional security features may be activated. In another embodiment, if no contact to sensing devices (e.g., medical/wearable devices) can be established, if these devices cannot be detected, etc. the additional security features may be activated.

The additional security features may be activated in phases, or they may be activated all at once. For example, starting from the time from a failed authentication, failure to connect or detect with sensing devices, etc., for a time period within a first time period (or threshold), the biometrics ID module/device may activate a first level of additional security features, such as full encryption and an additional security mode for biometrics profile data. In one embodiment, the biometrics ID module/device may request additional biometric modalities requested and may cross-check these modalities.

After the expiration of the first period, but before the expiration of a second time period (or threshold), the biometrics ID module/device may activate a full lock-down of all biometric data. The biometrics ID module/device and system may have a collection of security configurations sorted with increasing levels of security to protect users biometrics, financial, personal or other type of information. In each stage, the user's biometrics and other data is used to build confidence. If the requirements are not met, then a more conservative set of security rules may be activated (e.g., data encryption strength is boosted, sensitive data may be erased, device may contact server for lost/stolen device notification, etc.).

After the expiration of the second period, but before the expiration of a third time period (or threshold), the biometrics ID module/device may erase any digital certificate(s) and delete all biometric and other data.

In one embodiment, if the biometrics ID module/device detects that it was reported as lost or stolen, the biometrics ID module/device may erase all biometric data, personal data, and delete all security certificates. In one embodiment, the biometrics ID module/device may flash any ROM memory to remove any "hardwired" user personal data.

In one embodiment, the biometrics ID module/device may report its GPS location, WiFi location, cellular location, etc. to the server.

The additional security features, order of implementation, time periods for implementation, and number of phases in which the additional security measures may be implemented may vary as is necessary and/or desired. In one embodiment, the additional security features, order of implementation, time periods for implementation, and number of phases may be customized by a user, the user's organization, etc.

Figure 7:
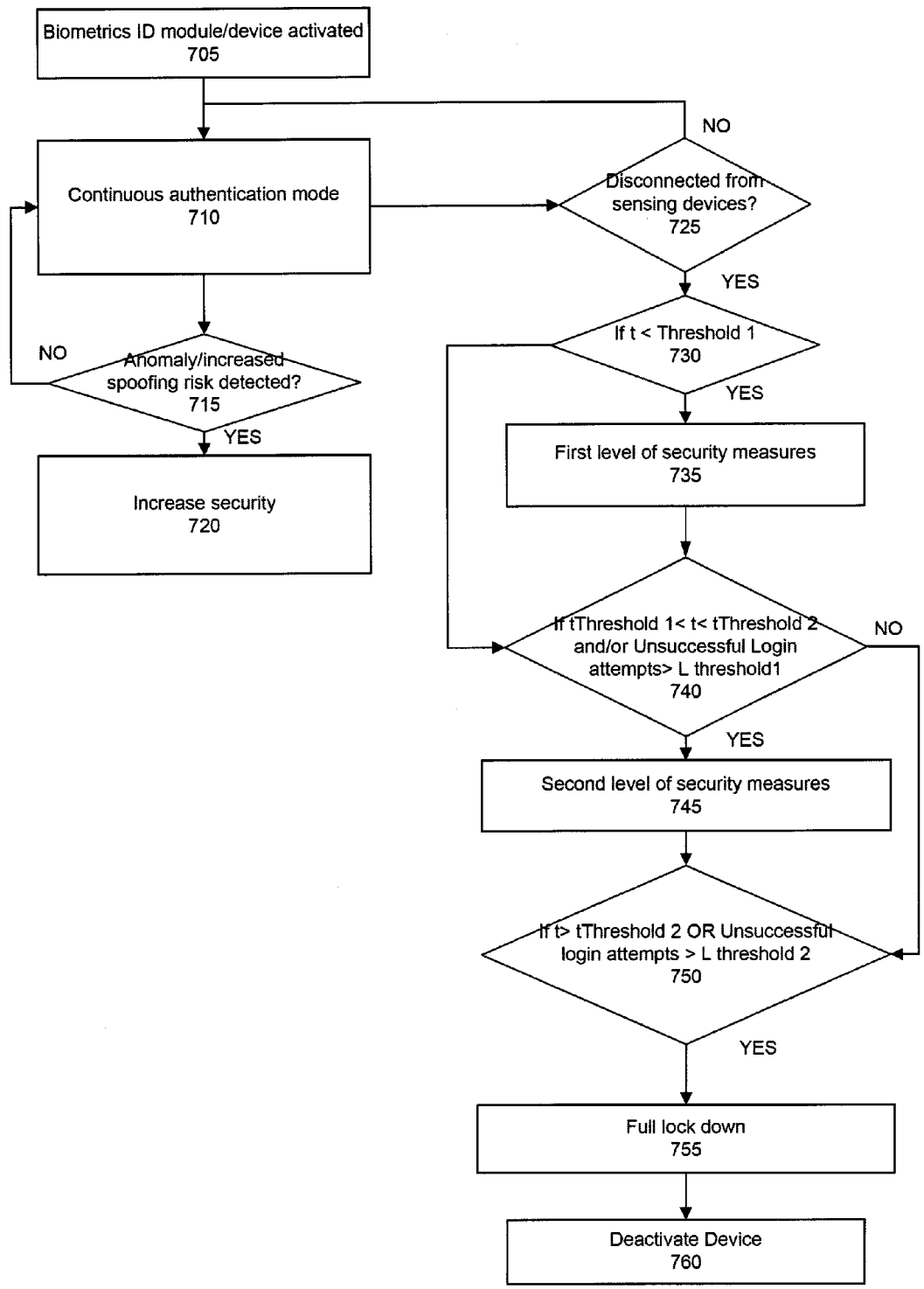
FIG. 7 is a flowchart depicting a method for implementing additional security features in a biometrics ID module/device.

Referring to FIG. 7, a method for implementing additional security features in a biometrics ID module/device is disclosed.

In step 705, the biometrics ID module/device may be activated and may be connected to sensing devices, such as biometric sensing device, medical devices, the user's personal devices, etc.

In step 710, a continuous authentication mode may be activated. This may include, for example, constant data collection (or substantially continuous data collection) from sensing device, user identification (e.g., voice recognition from a user device, such as a phone, iris recognition from smart glass, EKG from smart watch, etc.

In one embodiment, the collected data may be checked against a user profile, the last data collected, etc. for anomalies, spoofing risk, etc.

In step 715, if an anomaly or increased spoofing risk is not detected, the monitoring continues. If an anomaly or increased spoofing risk is detected, then in step 720, the biometrics ID module/device may require explicit biometrics authentication from user, such as an iris scan, face scan, voice biometric check, fingerprinting, etc.

During the monitoring, if, in step 725, a disconnection (e.g., out of range and cannot be detected, cannot connect, etc.) between the biometrics ID module/device and the sensing devices, additional security measures may be implemented.

In step 730, in a first time period, (i.e., within threshold 1), in step 735, the biometrics ID module/device may disable transaction mode, require higher strength encryption biometric profile data, and may request additional biometric modalities requested from user and cross-check that data. Additional, or fewer, security measures may be implemented as necessary and/or desired.

In step 740, in a second time period, or if the number of unsuccessful login attempts exceeds a first number, the biometrics ID module/device may implement a full lock down of all biometric data, activate higher security requirements (e.g., increased encryption, number of security steps increased), block access to the biometrics ID module/device (e.g., require connection to the server), perform a GPS check, require an online full biometrics check, etc. Additional, or fewer, security measures may be implemented as necessary and/or desired.

In step 750, in a third time period, or if the number of unsuccessful login attempts exceeds a second number, in step 755 the biometrics ID module/device may implement a full lock down of all biometric data, erase all biometric data and digital certificates, send a lost or stolen message to the server, provide its GPS, WiFi, and/or cellular location to the server, etc. The biometrics ID module/device may use its sensors to capture video, audio, temperature, etc. Additional, or fewer, security measures may be implemented as necessary and/or desired.

In step 760, the biometrics ID module/device may be fully deactivated and prevented from server access.

Figure 8:
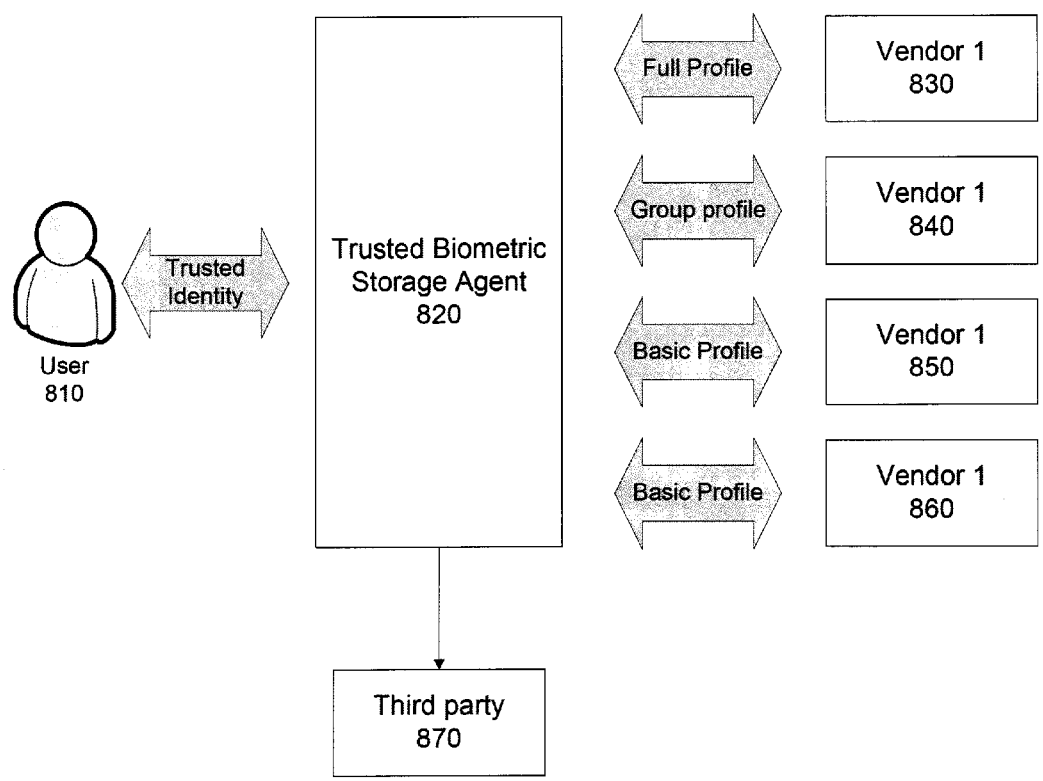
FIG. 8 is a block diagram depicting a system for independent approval and release of biometric data according to one embodiment.

In another embodiment, a system for independent approval and release of biometric data is disclosed. Referring to FIG. 8, user 810 may have a trusted relationship with trusted biometric storage agent 820. In one embodiment, trusted biometric storage agent 820 may be a bank, a financial institution, a security company, a government agency, etc. Trusted biometric storage agent 820 may receive and store user 810's biometric data and/or other personal data (sensitive and/or nonsensitive). In one embodiment, trusted biometric storage agent 820 may also serve as an intermediary between user 810 and vendors 830-860. Depending on the trustworthiness of each of vendor 830-840, trusted biometric storage agent 820 may release user 810's full biometric profile (e.g., to a trusted vendor), a group profile to a less trusted vendor, and only a basic profile to an untrusted vendor.

In one embodiment, the amount of biometric data that is released may be specified by user 810, by the relationship between trusted biometric storage agent 820 and vendor 830-860.

In one embodiment, user 810 may develop and sell his or her biometric profile to, for example, third party 870. User 810 may also delete his or her profile.

The disclosures of the following are hereby incorporated, by reference, in their entireties: U.S. Pat. Nos. 8,028,896 and 7,117,365; U.S. patent application Ser. Nos. 14/010,061; 13/908,618; 13/940,799; 61/844,097; 13/492,126; 13/297,475; 11/337563, 12/534,167; 10/867,103; 12/715,520; 10/710,315; 10/710,328; 11/294,785; and U.S. Provisional Patent Application Ser. Nos. 61/861,690; 61/866,572; 61/861,690; 61/861,676; 61/820,917; 61/823,669.

Hereinafter, general aspects of implementation of the systems and methods of the invention will be described.

The system of the invention or portions of the system of the invention may be in the form of a "processing machine," such as a general purpose computer, for example. As used herein, the term "processing machine" is to be understood to include at least one processor that uses at least one memory. The at least one memory stores a set of instructions. The instructions may be either permanently or temporarily stored in the memory or memories of the processing machine. The processor executes the instructions that are stored in the memory or memories in order to process data. The set of instructions may include various instructions that perform a particular task or tasks, such as those tasks described above. Such a set of instructions for performing a particular task may be characterized as a program, software program, or simply software.

As noted above, the processing machine executes the instructions that are stored in the memory or memories to process data. This processing of data may be in response to commands by a user or users of the processing machine, in response to previous processing, in response to a request by another processing machine and/or any other input, for example.

As noted above, the processing machine used to implement the invention may be a general purpose computer. However, the processing machine described above may also utilize any of a wide variety of other technologies including a special purpose computer, a computer system including, for example, a microcomputer, mini-computer or mainframe, a programmed microprocessor, a micro-controller, a peripheral integrated circuit element, a CSIC (Customer Specific Integrated Circuit) or ASIC (Application Specific Integrated Circuit) or other integrated circuit, a logic circuit, a digital signal processor, a programmable logic device such as a FPGA, PLD, PLA or PAL, or any other device or arrangement of devices that is capable of implementing the steps of the processes of the invention.

The processing machine used to implement the invention may utilize a suitable operating system. Thus, embodiments of the invention may include a processing machine running the iOS operating system, the OS X operating system, the Android operating system, the Microsoft Windows™ 8 operating system, Microsoft Windows™ 7 operating system, the Microsoft Windows™ Vista™ operating system, the Microsoft Windows™ XP™ operating system, the Microsoft Windows™ NT™ operating system, the Windows™ 2000 operating system, the Unix operating system, the Linux operating system, the Xenix operating system, the IBM AIX™ operating system, the Hewlett-Packard UX™ operating system, the Novell Netware™ operating system, the Sun Microsystems Solaris™ operating system, the OS/2™ operating system, the BeOS™ operating system, the Macintosh operating system, the Apache operating system, an OpenStep™ operating system or another operating system or platform.

It is appreciated that in order to practice the method of the invention as described above, it is not necessary that the processors and/or the memories of the processing machine be physically located in the same geographical place. That is, each of the processors and the memories used by the processing machine may be located in geographically distinct locations and connected so as to communicate in any suitable manner. Additionally, it is appreciated that each of the processor and/or the memory may be composed of different physical pieces of equipment. Accordingly, it is not necessary that the processor be one single piece of equipment in one location and that the memory be another single piece of equipment in another location. That is, it is contemplated that the processor may be two pieces of equipment in two different physical locations. The two distinct pieces of equipment may be connected in any suitable manner. Additionally, the memory may include two or more portions of memory in two or more physical locations.

To explain further, processing, as described above, is performed by various components and various memories. However, it is appreciated that the processing performed by two distinct components as described above may, in accordance with a further embodiment of the invention, be performed by a single component. Further, the processing performed by one distinct component as described above may be performed by two distinct components. In a similar manner, the memory storage performed by two distinct memory portions as described above may, in accordance with a further embodiment of the invention, be performed by a single memory portion. Further, the memory storage performed by one distinct memory portion as described above may be performed by two memory portions.

Further, various technologies may be used to provide communication between the various processors and/or memories, as well as to allow the processors and/or the memories of the invention to communicate with any other entity; i.e., so as to obtain further instructions or to access and use remote memory stores, for example. Such technologies used to provide such communication might include a network, the Internet, Intranet, Extranet, LAN, an Ethernet, wireless communication via cell tower or satellite, or any client server system that provides communication, for example. Such communications technologies may use any suitable protocol such as TCP/IP, UDP, or OSI, for example.

As described above, a set of instructions may be used in the processing of the invention. The set of instructions may be in the form of a program or software. The software may be in the form of system software or application software, for example. The software might also be in the form of a collection of separate programs, a program module within a larger program, or a portion of a program module, for example. The software used might also include modular programming in the form of object oriented programming. The software tells the processing machine what to do with the data being processed.

Further, it is appreciated that the instructions or set of instructions used in the implementation and operation of the invention may be in a suitable form such that the processing machine may read the instructions. For example, the instructions that form a program may be in the form of a suitable programming language, which is converted to machine language or object code to allow the processor or processors to read the instructions. That is, written lines of programming code or source code, in a particular programming language, are converted to machine language using a compiler, assembler or interpreter. The machine language is binary coded machine instructions that are specific to a particular type of processing machine, i.e., to a particular type of computer, for example. The computer understands the machine language.

Any suitable programming language may be used in accordance with the various embodiments of the invention. Illustratively, the programming language used may include assembly language, Ada, APL, Basic, C, C++, COBOL, dBase, Forth, Fortran, Java, Modula-2, Pascal, Prolog, REXX, Visual Basic, and/or JavaScript, for example. Further, it is not necessary that a single type of instruction or single programming language be utilized in conjunction with the operation of the system and method of the invention. Rather, any number of different programming languages may be utilized as is necessary and/or desirable.

Also, the instructions and/or data used in the practice of the invention may utilize any compression or encryption technique or algorithm, as may be desired. An encryption module might be used to encrypt data. Further, files or other data may be decrypted using a suitable decryption module, for example.

As described above, the invention may illustratively be embodied in the form of a processing machine, including a computer or computer system, for example, that includes at least one memory. It is to be appreciated that the set of instructions, i.e., the software for example, that enables the computer operating system to perform the operations described above may be contained on any of a wide variety of media or medium, as desired. Further, the data that is processed by the set of instructions might also be contained on any of a wide variety of media or medium. That is, the particular medium, i.e., the memory in the processing machine, utilized to hold the set of instructions and/or the data used in the invention may take on any of a variety of physical forms or transmissions, for example. Illustratively, the medium may be in the form of paper, paper transparencies, a compact disk, a DVD, an integrated circuit, a hard disk, a floppy disk, an optical disk, a magnetic tape, a RAM, a ROM, a PROM, an EPROM, a wire, a cable, a fiber, a communications channel, a satellite transmission, a memory card, a SIM card, or other remote transmission, as well as any other medium or source of data that may be read by the processors of the invention.

Further, the memory or memories used in the processing machine that implements the invention may be in any of a wide variety of forms to allow the memory to hold instructions, data, or other information, as is desired. Thus, the memory might be in the form of a database to hold data. The database might use any desired arrangement of files such as a flat file arrangement or a relational database arrangement, for example.

In the system and method of the invention, a variety of "user interfaces" may be utilized to allow a user to interface with the processing machine or machines that are used to implement the invention. As used herein, a user interface includes any hardware, software, or combination of hardware and software used by the processing machine that allows a user to interact with the processing machine. A user interface may be in the form of a dialogue screen for example. A user interface may also include any of a mouse, touch screen, keyboard, keypad, voice reader, voice recognizer, dialogue screen, menu box, list, checkbox, toggle switch, a pushbutton or any other device that allows a user to receive information regarding the operation of the processing machine as it processes a set of instructions and/or provides the processing machine with information. Accordingly, the user interface is any device that provides communication between a user and a processing machine. The information provided by the user to the processing machine through the user interface may be in the form of a command, a selection of data, or some other input, for example.

As discussed above, a user interface is utilized by the processing machine that performs a set of instructions such that the processing machine processes data for a user. The user interface is typically used by the processing machine for interacting with a user either to convey information or receive information from the user. However, it should be appreciated that in accordance with some embodiments of the system and method of the invention, it is not necessary that a human user actually interact with a user interface used by the processing machine of the invention. Rather, it is also contemplated that the user interface of the invention might interact, i.e., convey and receive information, with another processing machine, rather than a human user. Accordingly, the other processing machine might be characterized as a user. Further, it is contemplated that a user interface utilized in the system and method of the invention may interact partially with another processing machine or processing machines, while also interacting partially with a human user.

It will be readily understood by those persons skilled in the art that the present invention is susceptible to broad utility and application. Many embodiments and adaptations of the present invention other than those herein described, as well as many variations, modifications and equivalent arrangements, will be apparent from or reasonably suggested by the present invention and foregoing description thereof, without departing from the substance or scope of the invention.

Accordingly, while the present invention has been described here in detail in relation to its exemplary embodiments, it is to be understood that this disclosure is only illustrative and exemplary of the present invention and is made to provide an enabling disclosure of the invention. Accordingly, the foregoing disclosure is not intended to be construed or to limit the present invention or otherwise to

We claim:

1. A biometric identification device, comprising:
   a personal identification module that stores a profile for a user;
   a static biometric identification module that stores a plurality of static user biometric characteristics for the user;
   a dynamic biometric identification module that receives a dynamic user biometric characteristic from a sensing device, the device remote from the dynamic biometric identification module and communicating with the dynamic biometric identification module using RF communication and being registered to the user;
   a transaction processing module that receives, from a third party, a transaction request for a transaction being conducted by the user with the third party, the transaction comprising at least one transaction characteristic; and
   a security engine comprising at least one computer processor that determines an amount of at least one of the static user biometric characteristics, the dynamic user biometric characteristics, and the profile required based on the at least one transaction characteristic;
   wherein the transaction processing module communicates the determined amount of the at least one of the static user biometric characteristics, the dynamic user biometric characteristics and the profile to the third party; and
   wherein the biometric identification device is associated with the user.

2. The biometric identification device of claim 1, wherein the biometric identification device communicates with a host device that comprises a computer processor.

3. The biometric identification device of claim 2, wherein the host device is a computer.

4. The biometric identification device of claim 2, wherein the host device is a smart phone.

5. The biometric identification device of claim 1, further comprising:
   a field programmable module.

6. The biometric identification device of claim 1, further comprising:
   a biometric data history table that may store a history of biometric activity.

7. The biometric identification device of claim 1, wherein the sensing device is a wearable medical device.

8. The biometric identification device of claim 1, wherein the sensing device is a wearable electronic.

9. A method for processing biometric information to conduct a transaction with a third party, comprising:
   a biometric identification device receiving a transaction request from a third party for a transaction being conducted by the user with the third party, the transaction comprising at least one transaction characteristic;
   the biometric identification device determining a target level of biometric authentication required to conduct the transaction based on at least one transaction characteristic;
   the biometric identification device determining an amount of at least one of static user biometric characteristics, dynamic user biometric characteristics, and a user profile required based on the at least one transaction characteristic necessary for the target level of biometric authentication;
   the biometric identification device retrieving the determined amount of the at least one of static user biometric characteristics, dynamic user biometric characteristics, and the user profile; and
   the biometric identification device transmitting the determined amount of the at least one of static user biometric characteristics, dynamic user biometric characteristics, and the user profile to the third party.

10. The method of claim 9, further comprising:
    prior to transmitting the determined information, the biometric identification device receiving approval from the user to transmit the determined information to the third party.

11. The method of claim 9, wherein the transaction characteristic comprises at least one of a transaction amount and a security level associated with the transaction.

12. The method of claim 9, wherein the transaction is an access to a restricted area.

13. The method of claim 9, wherein the biometric identification device comprises a computer processor.

14. The method of claim 9, wherein the biometric identification device communicates with a host device that comprises a computer processor.

15. The method of claim 9, wherein the determined amount of the at least one of static user biometric characteristics, dynamic user biometric characteristics, and the user profile is retrieved from local memory of the biometric identification device.

* * * * *